(12) United States Patent
Viel

(10) Patent No.: US 10,597,156 B2
(45) Date of Patent: Mar. 24, 2020

(54) CLEANING DRONE

(71) Applicant: Pierre Emmanuel Viel, Geylang (SG)

(72) Inventor: Pierre Emmanuel Viel, Geylang (SG)

( * ) Notice: Subject to any disclaimer, the term of this patent is extended or adjusted under 35 U.S.C. 154(b) by 33 days.

(21) Appl. No.: 15/565,414

(22) PCT Filed: Dec. 28, 2015

(86) PCT No.: PCT/EP2015/081301
§ 371 (c)(1),
(2) Date: Oct. 9, 2017

(87) PCT Pub. No.: WO2016/165793
PCT Pub. Date: Oct. 20, 2016

(65) Prior Publication Data
US 2018/0118337 A1    May 3, 2018

(30) Foreign Application Priority Data

Apr. 15, 2015 (FR) ...................................... 15 00787

(51) Int. Cl.
*B64C 39/00* (2006.01)
*A61L 2/10* (2006.01)
*B08B 5/02* (2006.01)
*G05D 1/00* (2006.01)
(Continued)

(52) U.S. Cl.
CPC .............. *B64C 39/024* (2013.01); *A61L 2/10* (2013.01); *B08B 1/002* (2013.01); *B08B 5/02* (2013.01);
(Continued)

(58) Field of Classification Search
CPC ......... B64C 39/00; B64C 39/024; A61L 2/10; B08B 1/00; B08B 1/002; B08B 5/00; B08B 5/02; G05D 1/00; G05D 1/0088
See application file for complete search history.

(56) References Cited

U.S. PATENT DOCUMENTS 6,907,336 B2 *   6/2005  Gray ................... A01B 69/008
                                                              172/2
9,265,187 B2 *   2/2016  Cavender-Bares ...... A01C 7/00
(Continued)

FOREIGN PATENT DOCUMENTS

| | | |
|---|---|---|
| CN | 203122289 U | 8/2013 |
| DE | 10 2013 101194 A1 | 8/2014 |
| EP | 2 929 897 A1 | 10/2015 |

*Primary Examiner* — Yonel Beaulieu
(74) *Attorney, Agent, or Firm* — Baker & Hostetler LLP

(57) ABSTRACT

A computer-implemented method for managing the flight of a drone comprising a physical treatment device, the method comprises the steps repeated over time of measuring the distance between the drone and an object present in the environment of the drone; adjusting the distance from the drone to the object according to predefined internal parameters; and performing a physical treatment on the object from the drone. Developments describe the management of distances to objects, surface tracking, object recognition, the installation of beacons in the environment, the use of on-board or remotely accessed sensors (e.g. position and contact sensors, cameras, motion detectors) and various types of treatment (e.g. cleaning, dusting, sterilization). Both software aspects (e.g. learning, central or distributed logic, autonomy, cooperation with floor robots) and system aspects (addition of a fan, brush, duster or germicidal lamp) are described.

16 Claims, 8 Drawing Sheets

(51) Int. Cl.
  *B64C 39/02* (2006.01)
  *B08B 1/00* (2006.01)
(52) U.S. Cl.
  CPC ........ *G05D 1/0088* (2013.01); *A61L 2202/11* (2013.01); *A61L 2202/16* (2013.01); *B64C 2201/024* (2013.01); *B64C 2201/027* (2013.01); *B64C 2201/126* (2013.01); *B64C 2201/127* (2013.01); *B64C 2201/141* (2013.01)

(56) References Cited

U.S. PATENT DOCUMENTS

| | | | |
|---|---|---|---|
| 9,582,002 B2 * | 2/2017 | Cavender-Bares | A01C 7/00 |
| 9,756,844 B2 * | 9/2017 | Groeneveld | A01M 17/00 |
| 2011/0276044 A1 * | 11/2011 | Brommer | G06K 19/0723 |
| | | | 606/32 |
| 2012/0237083 A1 * | 9/2012 | Lange | G06K 9/00805 |
| | | | 382/103 |
| 2014/0032020 A1 * | 1/2014 | Guyette | G01S 19/54 |
| | | | 701/3 |
| 2014/0246545 A1 | 9/2014 | Markov | |
| 2014/0303814 A1 | 10/2014 | Burema et al. | |
| 2015/0027044 A1 * | 1/2015 | Redden | A01G 22/00 |
| | | | 47/58.1 R |
| 2015/0201605 A1 * | 7/2015 | Groeneveld | A01M 17/00 |
| | | | 701/410 |
| 2016/0275801 A1 * | 9/2016 | Kopardekar | G08G 5/0043 |
| 2017/0359943 A1 * | 12/2017 | Calleija | A01B 79/005 |
| 2017/0374323 A1 * | 12/2017 | Gornik | G06T 7/0004 |
| 2018/0129879 A1 * | 5/2018 | Achtelik | G01C 5/00 |
| 2018/0215039 A1 * | 8/2018 | Sinyavskiy | G05D 1/0044 |
| 2018/0314268 A1 * | 11/2018 | Tan | G05D 1/0646 |

* cited by examiner

CLEANING DRONE

CROSS-REFERENCE TO RELATED APPLICATIONS

This application is a National Stage of International patent application PCT/EP2015/081301, filed on Dec. 28, 2015, which claims priority to foreign French patent application No. FR 1500787, filed on Apr. 15, 2015, the disclosures of which are incorporated by reference in their entirety.

FIELD OF THE INVENTION

The present invention relates to the technical field of robotics, and in particular to drones. More specifically, the invention relates to methods and systems for cleaning using a drone.

BACKGROUND

A drone or UAV (unmanned aerial vehicle) is an unmanned aircraft. A drone may be autonomous and/or remotely piloted.

The drones currently on the market vary widely in terms of performance, size, autonomy, operating costs and purchase price. Drones have both civil and military applications. Some drones are low-cost toys while others are professional models worth many thousands of euros. From a technological standpoint, n-copters such as quadcopters are the most widespread models on the market. Some drones are only a few centimeters in size (for example biomimetically inspired drones) while others have wingspans of several meters (e.g. combat drones). Certain drone ranges allow payloads to be transported. The majority of drones currently on the market include flight stabilization methods and devices. Although drone flight plans may sometimes be entirely predefined, they are generally at least partially remotely guided by a human operator.

The on-board instrumentation of drones has progressed substantially in recent years. For example, improved batteries now allow significantly increased flight autonomy, on-board processors are more powerful, providing faster feedback loops, and image acquisition sensors exhibit increased sensitivity, improving imaging and/or navigation. Furthermore entirely new capabilities have become envisageable, in particular by virtue of progress made in the field of MEMS (microelectromechanical systems), allowing improvements in gyroscopes, accelerometers and laser autofocus systems. Contemporary drones may also use new cameras providing depth information (depth-of-field cameras or time-of-flight cameras). In fact, drones have pervaded numerous fields of activity (surveillance, telecommunications, logistics, art, leisure, etc.).

However, the application of aerial drones to (domestic or industrial) cleaning still remains relatively underdeveloped.

For several years now there have been robotic vacuum cleaners limited to floor movements which replace conventional brooms and vacuum cleaners for the purpose of picking up dust, relieving the user of this chore. Some of these floor robots use random movements and/or map the rooms of the house (for example using cameras). The movement patterns of these machines are variable. Sometimes movement is entirely predefined, with local adaptations (e.g. reflex arcs) for appropriately adapting to unexpected occurrences and/or to obstacles (collision avoidance). However, user intervention is still frequently required: the latter generally has to facilitate access to certain surfaces or otherwise to put in place measures to prevent movement (e.g. to prevent access to certain types of carpets or to lamp stands, to avoid cables on the floor in the path of the robot, etc.). These interventions are generally manual. In the majority of cases, only horizontal surfaces are concerned.

Scientific publications and patent literature do not address, or address only cursorily, the technical problem consisting in cleaning surfaces and/or objects. In particular, the prior art does not specifically deal with the treatment of non-horizontal and/or non-planar surfaces, or else surfaces located at height, i.e. surfaces other than floors and similar wide horizontal surfaces. It is apparent that the technical problems to be solved for these surfaces which cannot be likened to the floor (bookshelves and objects of any form for example) are entirely specific. The technical solutions described in the context of (non-aerial) robots intended for washing the windows of buildings exhibit limitations, as do the technical solutions published for cleaning solar panels. Patent document CN203122289 exhibits limitations in particular in terms of payload and trajectory optimization.

There is a domestic and industrial need for treatment, in particular cleaning, methods and systems using a drone.

SUMMARY OF THE INVENTION

The invention describes a computer-implemented method for managing the flight of a drone, said drone comprising a physical treatment device, the method comprising the steps repeated over time consisting in measuring the distance between the drone and an object present in the environment of the drone; adjusting the distance of the drone from the object according to predefined internal parameters; and performing a physical treatment on the object from the drone. Developments describe the management of distances to objects, surface tracking, object recognition, the installation of beacons in the environment, the use of on-board or remotely accessed sensors (e.g. position and contact sensors, cameras, motion detectors) and various types of treatment (e.g. cleaning, dusting, sterilization). Both software aspects (e.g. learning, central or distributed logic, autonomy, cooperation with floor robots) and system aspects (addition of a fan, brush, duster or germicidal lamp) are described.

Advantageously, a drone according to the invention may treat or clean the objects present in a dwelling. A commercially available drone generates propulsion (when moving) and sustentation (force counteracting gravity allowing it to maintain equilibrium in terms of altitude) airflows, which airflows cannot be used in practice to completely remove the dust deposited on objects in a dwelling: the direction of the propulsion/sustentation airflow is substantially parallel and in the opposite direction to the vector of gravity. As such, the lateral flow of air is weak and in any case insufficient for cleaning or dusting objects placed in proximity in the environment of the drone.

Advantageously, certain embodiments of the invention determine the movements of the drone in space according to a "surface tracking" mode. This embodiment consists in particular in not allowing the drone to stray beyond a certain distance from any element in its immediate environment.

Advantageously, the embodiments of the invention free the user from having to use an implement such as a duster, a cleaning cloth or a dusting wipe.

Advantageously, the embodiments of the invention relieve the user of the task of dusting. Certain embodiments of the invention provide a "robotic duster" allowing the dust deposited on one or more objects to be displaced into the surroundings (for example the dust deposited on window blinds).

Advantageously, the embodiments of the invention may be implemented inside buildings. Under certain atmospheric conditions (for example in enclosed or indoor environments), the displaced dust may be deposited on the floor after a finite period of time, simply due to Earth's gravity. This naturally fallen dust may then (optionally) be collected by a vacuum cleaner robot (or any other collection system).

Advantageously, the invention may be implemented "indoors". The prevailing air circulation conditions inside buildings generally entail a relative absence of turbulence. However, contrariwise, the invention may be implemented outdoors (turbulent conditions may contribute to redistributing displaced dust into its immediate environment). The "indoors" or "outdoors" property may be indicated by the user and/or evaluated by the drone itself (e.g. on the basis of air mass movements for example). Outdoors movement generally requires aerodynamic flight qualities and a certain degree of speed/reactivity (reaction with respect to aerological elements), whereas indoors flight generally requires stability, immobility and precise obstacle detection.

DESCRIPTION OF THE FIGURES

Other features and advantages of the invention will become apparent with the aid of the description which follows and the figures of the appended drawings in which.

DETAILED DESCRIPTION OF THE INVENTION

Figure 1:
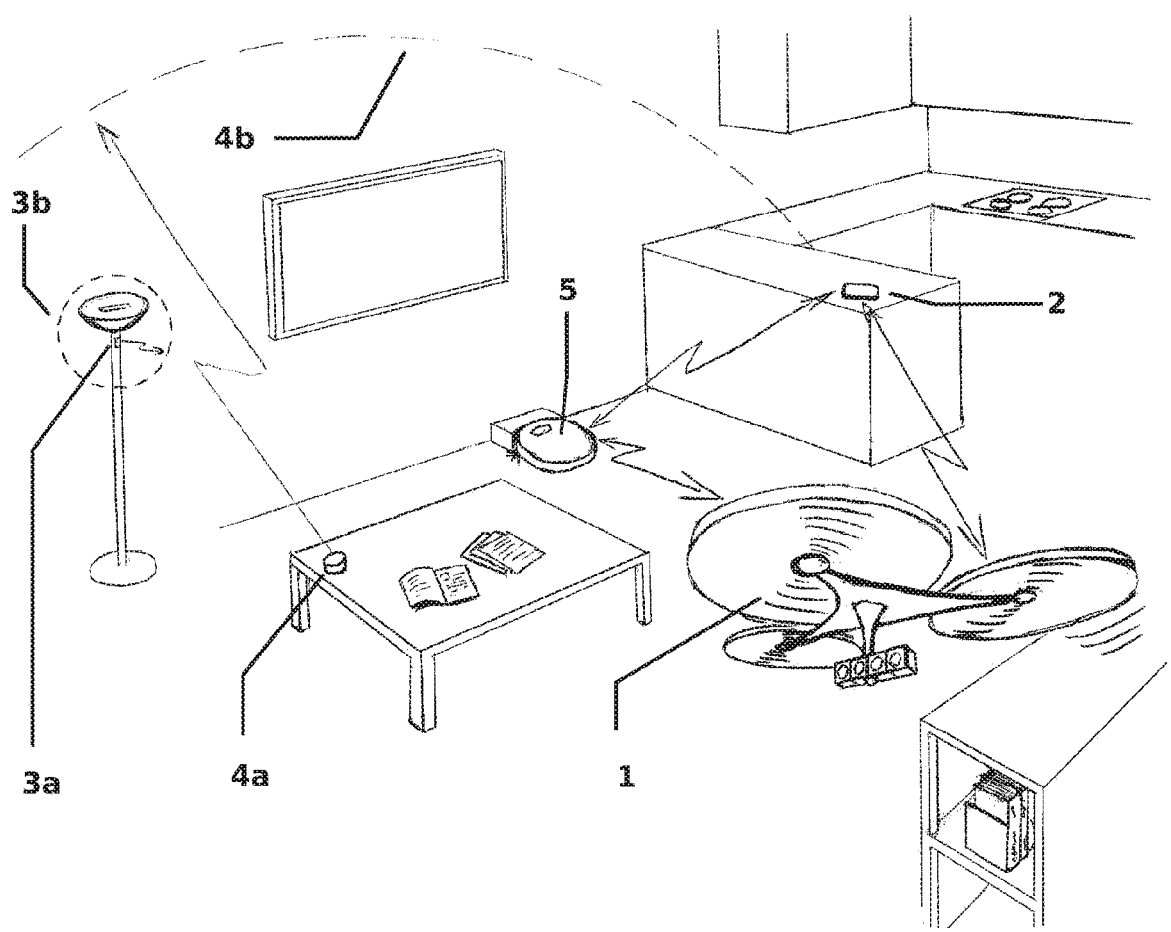
FIG. 1 shows an overall view of an exemplary system according to the invention comprising a drone, beacons, a vacuum cleaner robot and a computer for monitoring them all.

The term "surface" is understood to mean a wall formed from any material element (house walls, ornaments, etc.). In practice, a "surface" is determined on the basis of information gathered by the various sensors of the drone. In particular, data arising from the distance sensors that are optionally found on board a drone according to the invention make it possible to limit or to forbid flight trajectories of the drone that are located beyond a (predefined, configured or configurable) distance threshold from any surrounding surface. Stated otherwise, the distance threshold acts as a "virtual wall". This virtual wall makes the drone turn back toward surfaces from which it has strayed before it goes off on another trajectory on a state diagram.

The subjacent system used by the method according to the invention comprises at least one drone, which drone according to the invention is modified with respect to the prior art. The drone according to the invention comprises multiple permutations or variant embodiments, corresponding to specific technical features that differentiate it from a drone found on the market.

The drone implemented by the method is an "augmented" drone, i.e. a drone comprising additional technical features with respect to a drone known from the prior art. In particular, the drone possesses one or more physical treatment devices.

According to the embodiments, a "smart" (or "augmented", "home" or "home automation") drone is disclosed, which drone is configured to treat an object, a surface or a determined volume in the environment.

One or more drones modified according to the invention allow one or more treatments to be performed on one or more objects or surfaces present in the environment.

The surfaces may be surfaces present in a room of a dwelling, in an industrial workshop, in a factory, in a hospital, etc.

A plurality of drones according to the invention, of various sizes, may cooperate with floor robots.

In one embodiment, a "treatment" performed by a drone according to the invention comprises one or more cleaning operations (generically) and/or dusting operations (specifically), for example by projecting air or by friction or contact (electrostatic duster or brush). In particular, the cleaning or dusting operations may be more or less accurate and/or complete depending on the embodiment selected. In one embodiment, at least one drone may have chemical compounds on board (for performing a disinfection, painting or varnishing treatment) or else have means of a radiological nature on board (for example a UV disinfection lamp).

The treatments may be cumulative or combined (for example dusting and cleaning, washing and sterilizing, etc.).

In certain embodiments, the drone used by the method according to the invention has a wingspan of several meters (e.g. cleaning factories, ships or hangars). In other embodiments, a drone according to the invention has a wingspan of a few tens of centimeters (e.g. cleaning apartments, hangars or workshops). In other embodiments, a micro-drone according to the invention has a wingspan of a few centimeters (down to a few millimeters) (e.g. cleaning apartments as a swarm, treating a manufactured article, etc.).

Currently, the majority of micro-drones are larger than insects and fly with Reynolds numbers closer to those of the flight of birds. As such, a micro-drone according to the invention uses fixed wings and/or helices (or rotors).

In one embodiment, the micro-drone according to the invention flies with a lower Reynolds number (i.e. insect flight mechanics).

Generally speaking, there is a trade-off between wingspan (e.g. the number of rotors) and maneuverability: the larger the wingspan of the drone (the greater the number of rotors)

the more substantial payloads may be, but the less the drone is capable of performing "as close as possible" approaches to objects (e.g. in certain treatment situations such as sterilization, but while always respecting a minimum safety distance). In the majority of applications, "as close as necessary" approaches are performed, i.e. at a distance allowing the drone according to the invention to perform its treatment effectively.

In one embodiment, a single drone according to the invention is used. In other embodiments, a plurality or a swarm of drones may work in concert. In one embodiment, one or more drones according to the invention work in concert with one or more vacuum cleaner robots.

A drone used by the method according to the invention may be produced using various propulsion (flight) technologies.

The drone according to the invention may combine forward flight (e.g. fixed-wing aircraft) with hovering flight (for example helicopters and rotorcraft).

In certain embodiments, a drone according to the invention may be a trirotor or a quadrotor or else an n-copter, where n is greater than 4.

In certain embodiments, different movement means may be used, in combination with or instead of rotor propulsion. For example, the drone according to the invention may use one or more helium- (or any other lighter-than-air gas) filled volumes, for example in combination with one or more rotors. In certain embodiments, the drone does not need to be able to fly, or then not permanently: the method according to the invention may use a robot suitable for movement across vertical, or at least non-horizontal, surfaces (for example using a "gecko-robot" including one or more mechanisms for adhering to surfaces, whether or not the robot is capable of flying, for example intermittently or over short distances). The robotic system used by the invention may combine flight system and wall-adhesion features.

In one embodiment, the drone according to the invention comprises, in addition to the main propulsion device, a device for deflecting the airflow arising from this main propulsion system. This device allows the drone to clean i.e. to lift dust (dusting) laterally (to its sides), and hence to clean objects located at various elevations (ornaments on a shelf, books, etc.). The drone according to the invention may therefore in particular dust non-horizontal surfaces, but may also generate a less intense airflow than that used to propel the drone. This additional airflow deflection device is counter-intuitive in the context of the general use of a drone, where efficiency of propulsion is specifically sought (a non-coaxial airflow is not advised).

In one embodiment, in addition to or instead of an airflow defection system, the drone according to the invention comprises a device for generating an airflow, for example a fan, a blower or a blower bulb, which device generates a dedicated, generally transverse airflow, i.e. an airflow in a direction other than that of the axis of the propulsion airflow. This direction of the air from the fan may for example be substantially perpendicular to the main axis of propulsion, but variant embodiments envisage different configurations (for example at 30°). As above, this embodiment is counter-intuitive and therefore inventive. In a development of the invention, the fan of the drone is compensated for.

In one embodiment of the invention, in addition to the presence of the generation of airflows other than those from the propulsion or sustentation system, at least a portion of the rotors of the drone can be inclined.

In one embodiment, in addition to or instead of the devices described above, the drone according to the invention comprises a movable, immovable or removable portion that is intended to brush the surfaces to be dusted. For example, the drone may comprise a (passive or active, i.e. at least partially directable) electrostatic duster.

The flight trajectory of the drone is generally servo-controlled by the data gathered by a measurement device. Measurements are made continuously, regularly or at least intermittently. The drone generally possesses a measurement device (on-board sensors) but in certain embodiments the measurement means are solely present in the environment (for example a fisheye camera monitoring the movements of the drone).

A drone according to the invention may be endowed with various instruments in terms of measurement sensors, for example for measuring distance. In particular, the measurement of distances from the drone to objects in its environment is not necessarily performed by measurement instruments on board the drone itself.

In one embodiment, the drone is not endowed with any instruments, i.e. it does not include any proprioceptive sensors and can only be remotely piloted. The room in which the drone moves may be geometrically modeled by a system that is external to the drone (e.g. by a dome-shaped camera positioned in a room of an apartment, or else from video streams captured by one or more smartphones or cameras). This same system tracks the movements of the drone. The management of the appropriate distance from the drone to objects in its environment is then performed by software, according to the 3D model of the environment and of the movements of the drone. It carries out the servocontrol required for managing the trajectories of the drone inside the geometry thus determined. Advantageously, such a system only requires minimal intelligence on the part of the drone.

In other embodiments, a drone according to the invention observes and measures its environment by means of on-board sensors. Generally speaking, a drone endowed with instruments may use various methods (potentially in combination) for placing itself in its environment: by means of visual analysis (e.g. in the visible spectrum but also in the infrared, etc.), sonar (i.e. by propagating sound based on a variation in air pressure), radar or by means of an electro-optical method. It may record photographic and/or video trails.

In certain embodiments, the drone according to the invention comprises a set of sensors in order to ensure that the position and/or the distance of the drone with respect to objects and/or surfaces are maintained in accordance with flight rules (e.g. minimum distance, maximum distance, optimum distance, etc.).

In one embodiment, the drone according to the invention comprises one or more anemometers (for example laser velocimetry or laser Doppler anemometry). Measuring the movement of dust particles in the atmosphere or ambient air allows trajectory optimization.

According to the embodiments (cost factors, ease of integration, etc.), these sensors may comprise sensors using various technologies. The drone according to the invention may have combinations of sensors using various technologies on board. For example, one sensor may be a distance sensor using ultrasound (bursts of ultrasound), using sonar and/or using a stereoscopic camera or a camera providing depth information. A set of sensors (e.g. ultrasound sensors) may be installed on board the drone. In one variant embodiment, the drone may be provided with multiple sonars, in practice ultrasound emitters/receivers, arranged pairwise on each of the sides of the drone, thus producing a sonar "bubble" surrounding the drone. Within each pair, for a given side, the two sonars are spaced apart and have the same orientation, so as to provide stereo echolocation. Although the rotors return parasitic echoes, the signals that they reflect may be filtered out since they can be identified as being too close. In order to discriminate between variations in terms of echoes due to noise and to interference from variations due to a movement of the drone, the measurement may be based on samples sent by the sonar in order to identify whether the shift in the echoes follows a tendency or a random distribution. Certain sensors may be contact sensors positioned around the drone in order to ensure that the distance from the drone to surfaces to be dusted and to other surrounding surfaces is suitable or optimized in order to minimize disruptions to elements (objects, surfaces) other than dust. The drone may be endowed with sensors allowing it to detect the movement of elements other than dust in immediate proximity to the location in which it is found, in particular so that the system adjusts its operation when such movements begin to be perceived (e.g. movement of the object being dusted or cleaned). The sensors for detecting the movement of elements in immediate proximity to the drone may for example consist of visible spectrum or infrared cameras. Depth-of-field or TOF cameras may be supplemented or replaced by lighting systems (projection of a laser grid or of a simple light grid in order to evaluate volumes and deformations or movements, by analyzing changes in the scene under evaluation, compensating for movements caused by movements of the imagers, etc.).

In the context of the invention, the sensors make it possible to servocontrol the spatial position, i.e. to position the drone at a distance $d_{optimale}$ from surrounding elements, where $d_{min} < d_{optimale} < d_{max}$, $d_{max}$ is the distance beyond which the drone has strayed too far to carry out cleaning (e.g. dusting, washing, etc.) properly and $d_{min}$ is the distance short of which the drone risks being too intrusive, i.e. disrupting elements located in proximity.

The movements in space of the drone modified according to the invention are determined by the steps of a method specific to the invention.

According to the embodiments, the drone maintains a minimum and/or a maximum distance with respect to objects it approaches or over which it flies. In certain embodiments, an optimum distance is maintained.

The drone intrinsically possesses a given wingspan (referred to as the "residual", "intrinsic", "internal" or "contact" distance). In the case of a quadrotor, the wingspan corresponds to the dimension between opposite rotors (or the maximum dimension in case it is asymmetrical).

A drone is also associated with a "safety" distance corresponding to the sum of the wingspan and a safety margin, so that no contact is possible (or probable, in a variant) with the environment, besides via the dedicated accessories.

Maintaining a minimum distance has various consequences in terms of energy: the drone spends less energy on airflows for cleaning, however it spends more energy on following more detailed trajectories, following less approximately the details of the contours of the work environment.

The existence of a minimum distance also makes it possible to avoid getting too close to the environment and disrupting the latter by moving elements other than dust (sending paper flying, etc.). The minimum distance is necessarily greater than or slightly greater than the safety distance.

Maintaining a maximum distance prevents the drone from moving without purpose in the middle of rooms, since by definition no object to be dusted or cleaned is found levitating (i.e. every object is necessarily in contact with other objects, either contiguously or connectedly, e.g. walls, floor and ceiling included).

Maintaining a maximum distance (greater than the minimum distance, which is itself greater than the safety distance, itself greater than the wingspan of the drone) makes it possible to carry out "surface tracking" according to the invention (minimum cleaning efficacy).

Respecting a minimum distance and a maximum distance between the drone and the surfaces present in the environment may be achieved simultaneously, for example in the "surface tracking" embodiment.

In certain embodiments, a drone directly or indirectly possessing a map of the environment may (occasionally) not observe the maximum distance constraint, for example by allowing rooms to be crossed if this allows the cleaning plan to be optimized.

A minimum distance alone may be considered (the drone seeks to optimize the cleaning operation as far as possible but deviations may then take place toward the interior of the volume to be treated).

A maximum distance alone may be considered (the drone may then take risks and move as close as possible to objects modulo its own safety distance).

Lastly, optimized flight trajectory envelopes may be determined, seeking trade-offs between these various distances. For example, by means of 3D object recognition (or recognition of objects in 2D images, e.g. pattern matching) via the images acquired by its video sensors, the drone is able to determine the nature of the object in immediate proximity at a given instant in time and to adjust its trajectory according to this nature thus determined; faced with a book (for example determined as such by means of optical character recognition) the drone will approach as close as possible, while faced with an object categorized as fragile or uncategorized, the drone will adopt a safer flight trajectory by increasing the distance between itself and the object.

As the resolution of the environmental analysis of the drone improves, the relative constraints or demands on surface tracking may be softened (i.e. parameters, rules or constraints are relaxed, etc.). The system may learn from its prior passes in order to directly find the best distance obtained during preceding passes by analyzing the data returned by its sensors (if for example in a first pass the scene was identified as being easily "disruptable", thus obliging the drone to distance itself or to decrease the intensity of its dusting, this experience could be reused in a subsequent pass in order to directly adopt parameters that are closer to those obtained during the first pass).

Other embodiments are described hereinbelow. The distance between the drone and the closest object may be bounded (one, two or even n boundary markers). For example, the distance of the drone may be optimized between a minimum security distance (determined by the geometric wingspan of the drone) and a maximum distance (determined so as to perform an effective treatment on or in the direction of the object, i.e. according to quantified efficacy criteria). The trajectory envelopes ("virtual walls") may comprise a third boundary marker (optimum distance according to the projection that is orthogonal to the overflown surface of the environment). Other boundary markers may be defined (e.g. power management, safety distance with respect to human users, safety distance with respect to animals, safety distance with respect to the intensity of the airflow generated for sustentation, etc.). In this way, a veritable topology of trajectory envelopes may be defined, over which the flight management of the drone (or of the plurality of drones) implemented by the method according to the invention operates.

The drone approaches objects according to various parameters. The parameters may be predefined (for example factory-set approach distance). In addition or instead, the parameters may be determined by sensor feedback (for example minimum approach distance limited by the detection of movements due to the drone, such as those resulting from overly intense airflows, in the zone). In addition or instead, the parameters may be determined according to the object (for example by means of image recognition). In addition or instead, the parameters may be determined according to the environment of the drone (for example according to an environment in which beacons have been installed). The parameters may be determined according to one or more of these modalities. For example, the trajectories of the drone may be exclusively managed, governed, influenced or regulated by image recognition carried out by the drone. Certain parameters are implicit, for example the parameters associated with the drone comprise information relating to its geometry and hence to its maneuverability.

The flight management parameters of the drone may be static (e.g. stable, invariant or according to planned movements) and/or dynamic (e.g. according to the environment). The flight of the drone may be managed statically and dynamically (planned trajectory sequence, local adjustments, overall self-planning).

According to various embodiments, the environment in which the drone according to the invention moves may be endowed with various instruments.

The work environment may also not be endowed with instruments, for example if the user arranges the work environment (for example the first few times it is used, by removing or stabilizing the most fragile objects, by closing certain doors, etc.). In this embodiment, the environment is not endowed with instruments: the movements of the drone rely then on the on-board sensors alone.

In one embodiment, the environment is partially endowed with instruments (for example by the user him- or herself or preconfigured during construction, for example in a hotel room): one or more beacons (using various technologies which will be discussed below) delimit particular surfaces and/or volumes (e.g. to be avoided or to be cleaned as a priority for example). In certain embodiments, the environment may incorporate beacons defining or delimiting volumes to be avoided by the drone or volumes that the drone should not leave. The embodiments of the invention may specifically comprise beacons so that the drone does not approach locations that are deemed fragile, dangerous or unnecessary. Similarly, certain beacons may delimit spaces that the drone should not leave (e.g. safety zones or simply natural limits between rooms of a dwelling, etc.).

In one embodiment, the beacons may consist of transponders (also called labels, tags, markers, etc.) and RFID detectors, the detection range or intensity of which delimits a volume to be avoided or a volume that the drone should not leave.

In one embodiment, the beacons may be sound (e.g. infrasound, ultrasound) beacons. This type of beacon may be economically advantageous.

In one embodiment, the beacons may comprise one or more visual markers (e.g. QR code, Data Matrix, etc.), the size of which could have an effect with respect to their detection distance (i.e. depending on the characteristics of the on-board camera). This type of beacon entails almost no extra cost.

In one embodiment, one and the same beacon may also combine several of the technologies described above. For example, one and the same beacon could combine the use of a QR code and an RFID transponder.

In one embodiment, the method may use heterogeneous beacons (for example, certain beacons will be QR codes while others will be RFID transponders and still others will be sound and RFID hybrid beacons).

In certain embodiments, the beacons are non-hardware-based beacons, for example defined on the basis of logic and/or software by the user (designation of spatial coordinates e.g. by entering them manually into the software, using a laser pointer or any other augmented and/or virtual reality device means; for example the user designates or simulates the trajectories of the drone by virtually moving within the room using a virtual reality helmet and a haptic pointing device).

The drone according to the invention may exhibit various degrees of autonomy.

The "autonomy" of a drone covers various technical aspects. A drone is an unmanned aircraft. A human influence is always present to a greater or lesser degree, whether directly or indirectly, in time and/or in space, for example whether through commands (remote-piloting) and/or through program code (which will read and interpret data encoding trajectories).

A drone according to the invention may be autonomous, i.e. comprise the capability to navigate by itself. A drone according to the invention may be semi-autonomous (by delegating certain phases of flight to the machine). A drone according to the invention may be partially or entirely remote-piloted. A drone according to the invention may be successively or temporarily in one or the other of these states.

In one embodiment, the drone according to the invention is fully autonomous. It predetermines its movements, carries out local and real-time adjustments according to the data measured by its sensors, manages its battery power (e.g. the drone performs optimized return flights to the power source, etc.).

In certain embodiments, the drone according to the invention is partially autonomous: certain—for example instinctive—tasks do not require the intervention of the user. Other activities of the drone are for example supervised to a high level of abstraction by the user, who dictates for example general setpoints, for example in terms of priorities (e.g. priority given to the speed of cleaning, to the efficacy of cleaning or to power optimization, etc.) and/or in terms of zones (e.g. the expression "not in the kitchen" is transcribed into text, handled in the rules system then communication with the beacons is carried out, if necessary) and/or in terms of timetable (e.g. "I will be out until 4 o'clock"). Stated otherwise, vocal and/or visual and/or programming interfaces may allow general instructions to be received then converted into formal rules inside the treatment or cleaning system that the drone will be forced to follow.

A drone according to the invention may play back a predefined trajectory (including those involving tracking a target). A drone according to the invention may locally adjust its trajectory once an overall objective has been determined (e.g. tracking the relief of the floor). A drone according to the invention may determine its flight plan itself, having knowledge of a general objective (in this instance, cleaning or treating an object, a zone or a given volume).

In certain embodiments, the drone according to the invention is not autonomous (with the exception of flight stabilization per se): the drone is then (almost) entirely piloted by the user (either directly in the same room, or remotely via image acquisition means), modulo the mandatory safety distances since they aim to preserve the physical integrity of the drone itself.

In one embodiment, the user plans a trajectory (which results in the reception of a given trajectory) and the drone then refines this trajectory in order to position itself at the correct distance from the zones to be cleaned. Stated otherwise, the drone remains generally active in terms of local adaptations to its environment. Such a non-autonomous mode may be used if its movements remain limited by the maximum and minimum distance rules, thus defining a virtual corridor only within which the drone may be maneuvered by the user (within the programming interfaces, encountering virtual walls may result in vibrations; it is also possible to oppose a force when the user wishes to carry out a command outside of the permitted range).

In one embodiment, the exemplary maximum and minimum distance rules may also be applied after a trajectory acquisition step by the user, the drone then adjusting the trajectory provided in order to adhere to the constraints. (Referred to as "teaching" mode, described below.)

The degrees of autonomy of the drone are configurable.

The autonomy of the drone may be reconfigured in real time: the user may for example take (back) control of the movements of the drone when he or she desires (disengageable autonomy). The movements of the drone in space may be planned in terms of time and/or in terms of space.

The set of rules upon which the movements of the drone in three-dimensional space are conditional are configurable. These rules may be predefined (when the drone according to the invention is commercially available, it may comprise a set of rules defined by default). One or more of these rules may be modified by the user, including in real time.

The rules governing the movement of the drone in space comprise in particular rules relating to safety distances (e.g. movements within a defined zone in order to pass by and/or stop at a suitable distance from various surfaces, whether horizontal or not, that are liable to accumulate dust), rules for adjusting the stationary flight distance from objects to be cleaned (e.g. this distance being optimized in particular for displacing only the dust deposited on the object), rules relating to the duration of flights between two power recharging operations, rules for movement within volumes (e.g. the steps of the method consist in particular in substantially tracking surfaces rather than moving toward the center of volumes in order to optimize power consumption by the drone), rules relating to unwanted noise (e.g. minimum distances with respect to users, the presence of which is for example determined by means of facial detection in the image streams captured by the drone), rules relating to cleaning per se (e.g. starting the cleaning operation at height or at the maximum allowed height and gradually decreasing in flight altitude toward the floor, in a confined environment for example), rules for operating in conjunction with other robots (e.g. swarm, fleet, collection or plurality of aerial drones, coupled with one or more floor vacuum cleaner robots; these rules may for example relates to the various cleaning sequences, alternating floor cleaning and the cleaning of other surfaces).

In one embodiment of the invention, the autonomy of the drone can be "disengaged", meaning that it is possible for the user to take control of its movements (referred to as "semi-autonomous" mode). In practice, the user may use a dedicated remote controller or an electronic device running the instructions of a code or suitable computer program (app). Advantageously, the user may thus concentrate on a particular zone or deal with an area that has been "forgotten" or insufficiently treated by the invention.

In one embodiment of the invention, learning exercises are carried out in order to "plan" the cleaning operation. These learning exercises may be supervised or else unsupervised (i.e. user intervention remains optional, e.g. machine learning or deep learning). In one embodiment, the user indicates to the drone or to the software application which zones are to be cleaned and/or the sequences in which treatment is to be performed.

These learning exercises may take place according to various modalities. Trajectory instructions (or trajectory portions) may be recorded in various ways, for example by projecting a laser or luminous flux into the room, by using an augmented and/or virtual reality device, by drawing within a dedicated software application or using a remote controller. The user may also take the drone by hand and walk it through the most suitable trajectories, which drone will record the corresponding spatial coordinates. Learning modes may be combined.

Trajectories may first be marked out roughly or schematically: they may be finely optimized by the drone later on, for example according to sensor data. For example, in one embodiment of the invention, the user describes a simple trajectory to the drone by passing close by zones to be dusted. When this simple trajectory is played back, the system, which retains a representation thereof, locally adjusts it according to information on the immediate environment of the drone that the sensors of the drone return to the latter. Thus the drone, while following the direction indicated by this trajectory overall, will locally deviate therefrom in order to position itself at a suitable distance from the surfaces to be dusted. In addition to simplicity of handling for the user, this embodiment also has the advantage of making it possible to adapt to local changes in the environment (such as for example an object having been moved).

Trajectories may be marked out in portions: for example, only "complex" zones (including many objects) may be subject to manual learning.

In one embodiment, a prior map is received by the drone and/or determined thereby (either wholly or in part; cf. SLAM (simultaneous localization and mapping) algorithms), in order to rationalize movements in the zone to be covered.

The map may be a prior map and/or a map produced in real time. For example, it may be determined by the drone. The map may also be used by the drone, after having been established remotely. The drone may also respond to trajectory commands without having direct access to a map (i.e. decentralized and/or distributed master software may send only commands to a slave drone; the master software may fully determine where the drone is located, for example according to previously sent commands and information on local modifications made to the commands, which in one embodiment are retransmitted to the master software).

Its knowledge of the environment allows the software then to relax the surface tracking criterion so that, for example, the drone is no longer obliged to creep alongside walls in order to move from one location to be dusted to another (for example, the creation of a 3D map using the SLAM algorithm makes it possible to identify the walls of a room as the outer limits of a map when the latter is viewed from above, and hence to tag the elements that are located between these walls and which also constitute locations to be dusted).

The methods and systems according to the invention may be physically and/or logically coupled with one or more robot vacuum cleaners.

In one embodiment, coupling may be direct (i.e. communication takes place directly with the one or more robot vacuum cleaners, without the action of an intermediate regulator). In one embodiment, coupling may be indirect, i.e. take place via other peripherals (for example a smartphone, which constitutes the central regulating member). In certain embodiments, the regulation of the actions carried out by one or more floor robots and/or one or more drones according to the invention may entail direct and/or indirect communications via regulating entities (e.g. amplification, reduction, filters, prioritization, placing in a waiting line, caching, time shift, etc.).

The regulation of the overall system (floor robots and drones according to the invention), in other words orchestrating the various cleaning sequences of the various cleaning machines and the various charging phases of the devices, may be ensured by implementing steps (i.e. software layer) carried out by the one or more drones and/or the one or more robot vacuum cleaners and/or by one or more intermediate peripherals.

The invention synergetically combines hardware elements (system) and software elements (method).

The computer program or code implementing the method according to the invention, for managing the trajectories and the treatment/measurement operations of the drone, may be installed on board (i.e. inside the drone itself) or remote (i.e. accessible at distance). The drone may be autonomous, semi-autonomous (the user may take control of the movements of the drone), or else remotely piloted.

The trajectories of the drone may be planned (for example when the user indicates to the system how to link together the zones to be dusted). The distance from objects may be adjusted by default (statically, for example by a distance adapted to the various surfaces that are liable to accumulate dust) or dynamically (e.g. by adapting the distance so as to displace said dust while avoiding displacing other things).

One or more steps of the method according to the invention are implemented by computer so as to determine (e.g. calculate) the trajectories of the drone in space.

The computing (e.g. CPU, GPU) and/or storage (e.g. mass storage) and/or memory (e.g. ROM/RAM) means may be physically centralized or distributed (e.g. implemented in the drone itself and/or in one or more home or home automation servers and/or in one or more remotely accessed servers (cloud computing) and/or in a home vacuum cleaner robot and/or in a smartphone or home computer, etc.).

For example, the "intelligence" may be shared between the home vacuum cleaner robot and the aerial drone according to the invention. In another embodiment, this intelligence is centralized in the smartphone of the user, or else in a cloud computing-type online service.

In one embodiment, the drone includes one or more SoCs (system on chip) (i.e. a chip grouping together a main processor, a graphics processor, for example suitable for computing certain SLAM functions, along with other circuits) in order to perform all or some of the treatment operations required by its task. In addition or instead, one or more FPGA (field-programmable gate array), DSP (digital signal processor) or ISP (image signal processor) or an ASIC (application-specific integrated circuit) circuits may be used. Advantageously, an SoC and/or an FPGA and/or a DSP or an ISP and/or an ASIC may perform rapid computations, thereby providing the drone according to the invention with improved reactivity.

In one embodiment, a computer-implemented method for managing the flight of a drone is disclosed, said drone comprising a physical treatment device, the method comprising the steps repeated over time consisting in measuring the distance between the drone and an object present in the environment of the drone; adjusting the distance of the drone from the object according to predefined internal parameters; and performing a physical treatment on the object from the drone. In one embodiment, the distance between the drone and an object in the environment is "measured" (or "determined", i.e. by the drone itself or by one or more measurement devices external to the drone). This measurement is made with error margins, like any measurement (the measurement unit is unimportant, since it is conventional). The measurement may be made directly but may also be made indirectly. In the case of a drone endowed solely with contactors, the "measurement" is made in a specific manner (the detection of contact indirectly measures the distance from the object). In one embodiment, the distance is "evaluated", "estimated" or "approximated", i.e. the distance measurement is made quickly, potentially in a degraded manner (accuracy of measurement is not necessarily always required).

The internal or intrinsic parameters comprise general or generic parameters, in particular parameters associated with the wingspan and/or safety distances (with margin), parameters resulting from prior choices aiming to minimize the power consumption of the drone, etc. These parameters are generally predefined, i.e. factory set.

The object is generally immobile. In certain embodiments, the object may be mobile (e.g. an assembly line following a predictable trajectory for example). The drone then adjusts its overall trajectory and its relative movements.

In one development, the adjustment of the distance from the drone is additionally dependent on external parameters associated with an object present in the environment.

The external parameters comprise contextual data, i.e. relating to the environment (and its objects).

The external parameters comprise for example data relating to the environment endowed with instruments, if applicable (e.g. distances dictated by beacons, i.e. communicated by the environment or the object to the drone, either directly or indirectly).

The external parameters may also comprise parameters obtained by one or more feedback/servocontrol loops: the drone and/or its control system may interpret the environment of the drone and in particular monitor or quantify the effects of the drone on its environment (as the drone perceives them with its own instrumentation or as the master control system communicates them to the drone). According to these external parameters, the drone may move away from/closer to the object and/or increase/decrease the intensity of the treatment as soon as the perceived scene is determined as being excessively disrupted beyond a predefined threshold.

In one development, the external parameters associated with the object comprise a maximum distance beyond which the physical treatment performed by the drone on the object is below a predefined threshold.

The predefined threshold relating to the efficacy of the physical treatment (i.e. the maximum distance) may be constant or else variable depending on the one or more objects located in proximity.

The "surface tracking" mode observed by the drone may consist in not allowing the drone to stray beyond a certain distance from any element in its immediate environment. This maximum distance may correspond to the efficacy limit of its action.

Efficacy may be quantified, in particular by thresholds for detecting motion within images collected by the drone and/or by the control system and/or an array of sensors (e.g. the page of a magazine beginning to lift, an ornament beginning to wobble, etc.).

In one embodiment, the drone may fly "as close as necessary" to surfaces, i.e. i) as close as possible given its geometric wingspan and safety margin data and ii) so as to optimize the efficacy of the treatment performed by the drone. For example, the drone may fly alongside walls: not too close, to avoid damaging objects positioned on bookshelves for example, but not too far away, so as not to be ineffective in terms of treatment or cleaning. Adversely minimizing the flight distance from surfaces may entail a lengthening of trajectories (cf. the fractal figures), be overly intrusive, entail an overly powerful and/or overly local airflow, etc. Advantageously, trajectory envelopes are therefore determined while considering a lower distance boundary from objects.

In one development, the external parameters associated with the object are determined by object recognition.

The parameters comprise for example information relating to objects (object type e.g. book, vase, painting, etc.; properties e.g. stable, fragile, precious, etc.) and/or to the associated treatment (treatment type e.g. dusting, sterilization, etc.; treatment intensity e.g. soft, hard, speed, reiterations, etc.).

Object recognition may be performed in various ways, potentially in combination. An object may be recognized by image recognition (object in the image or in a video frame, e.g. pattern matching). An object may be recognized logically or actively (for example, the object may advertise its presence using beacons). Recognition may be performed locally (means installed on board the drone) and/or remotely (ceiling cameras, home automation server, smartphone, connected object, etc.).

In one development, the external parameters are determined after receiving the signal from one or more radiofrequency beacons placed in the object or the environment.

In one embodiment, a radiofrequency beacon emits a signal (directly) representing a fixed or predefined numerical value (passive tag). For example, a beacon associated with a halogen lamp will forbid the drone from entering into a zone that is dangerous for the drone and/or for the halogen lamp. In one embodiment, the signal emitted by a beacon, and/or its intensity, may be configurable and/or configured (e.g. an interpretation step could differentiate between drone models) or centralized logic could adjust the volume zones defined by "active" or programmable tags.

The beacon may be incorporated in (e.g. taped to, bonded to, inserted into the bulk of, etc.) the objects themselves, or in proximity thereto. The beacon delimits the space of the possible trajectories of the drone. The radiofrequency beacon may be an RFID transponder or tag for example. Beacons positioned in the environment make it possible, according to the type of each one and/or the choice that is made for each one, to delimit volumes to be avoided by the drone or volumes that the drone should not leave.

The beacon may also define cleaning parameters of the object with which it is associated.

In one development, the physical treatment performed on the object by the drone comprises one or more treatments chosen from a dusting treatment and a sterilization treatment.

In one embodiment, the drone according to the invention has neither a collector nor a reservoir (the limited payload of the drone is dedicated to active instrumentation that does not require the transport of liquid, solid or gas, at least in significant amounts). A swarm of drones according to the invention cooperating on one and the same treatment task may multiply the journeys made for collecting a payload (for example paint), at least partially avoiding the need to transport substantial payloads.

For sterilization, in one embodiment, the drone according to the invention comprises an ultraviolet lamp (germicidal lamp). An ultraviolet lamp is a bulb that transmits ultraviolet radiation through a medium that it is desired to be sterilized without negatively affecting its properties. A germicidal lamp is a lamp that emits ultraviolet radiation with a wavelength of 253.7 nm. This ultraviolet light ionizes oxygen and produces ozone, which can eliminate many pathogenic germs.

In one development of the invention, a drone according to the invention has neither a reservoir nor a collector (of significant size) but is linked thereto, for example by means of one or more tubes or hoses. In one development of the invention, a drone according to the invention additionally comprises means for connection to a reservoir (which may be independent, fixed to the ground or partially movable), the reservoir containing compounds such as paint, perfume, fertilizer, varnish, etc.). In one embodiment, the connection means comprise one or more hoses or tubes. In one embodiment, the connection means may be disconnected and reconnected from one drone to another drone (drones according to the invention may alternate with each other across spatial cells). In one embodiment, a drone may be disconnected from one connection means in order to be reconnected to another connection means so as to vary the type of treatment. In one embodiment, the reservoir is borne by a floor robot and the trajectories of the drones and of the reservoir are harmonized. In one embodiment, a plurality of reservoirs on the floor is addressed by a plurality of drones according to the invention. In one embodiment, the reservoir is a reservoir borne by a "tanker drone" (which is generally stationary but capable of moving and/or of landing intermittently).

In such configurations, the physical treatment performed on the object by the drone may comprise one or more operations from a watering (water, liquid), washing (water, liquid), waxing (wax), varnishing (varnish), buffing (liquid), painting (liquid), insect-removal (liquid or gas insecticide), misting (water, liquid), decontamination (liquid, solid or gas decontaminant), dusting (collector), disinfection (liquid or gas disinfectant) or dry-cleaning (water, steam) operation. In one particular embodiment (automatic watering of plants), one or more drones according to the invention may be connected to the watering hose of a garden for example so as to be able to take turns in watering said garden.

In one development, in addition or instead, the drone according to the invention comprises a reservoir configured to receive one or more liquids and/or gases. In addition or instead, the drone comprises a collector.

A computer program product is disclosed, said computer program comprising code instructions allowing one or more of the steps of the method to be carried out.

A system is disclosed comprising means for implementing one or more steps of the method.

A system is disclosed comprising at least one drone, the drone comprising a physical treatment device for dusting and/or sterilizing one or more objects present in the environment.

In one development, the drone comprises, besides its propulsion system, a physical treatment device comprising a device for generating an airflow in a direction that is substantially non-parallel to the axis of sustentation and/or of propulsion of the drone.

In one development, the drone comprises one or more devices for generating airflows that are arranged so as to allow static or dynamic equilibrium in terms of force and/or in terms of moment.

In one development, the drone comprises a measurement device configured to allow the distance between the drone and an object present in the environment to be adjusted.

The drone may have a measurement device (e.g. sensors) on board. Alternatively, the measurement device may be remote or remotely accessed (e.g. one or more ceiling cameras).

In one development, the measurement device comprises at least one sensor selected from a position sensor, a contact sensor and a motion detection sensor. In one development, the measurement device comprises a combination of multiple sensors selected from position sensors, distance sensors, contact sensors and sensors for detecting motion.

In one development, the measurement device comprises a camera.

The distance measurement may be made by using an RGB-D camera (on board the drone or placed in the environment). The distance measurement may also be made by using ultrasound, LIDAR-type lasers, etc. Advantageously, the measurement of the distance from objects may be made by VSLAM using an inexpensive standard camera (i.e. a non-RGB-D camera).

In one development, the physical treatment device comprises at least one fan.

In one development, the physical treatment device comprises a motorized brush and/or a duster.

The duster may be an electrostatic duster.

In one development, the physical treatment device comprises a sterilizer or a germicidal lamp.

In one development, the drone is autonomous.

In one development, the system according to the invention comprises a plurality of drones.

In one development, the system additionally comprises at least one floor-cleaning robot.

In one embodiment, the system comprises one or more drones according to the invention operating in conjunction with at least one robot vacuum cleaner and its charging base station, characterized in that the system is physically and/or logically coupled with the robot vacuum cleaner or with its charging base station, either directly or via other peripherals, so that the zones of activity and/or phases of activity and/or respective operations of recharging the robot vacuum cleaner and of the one or more drones are managed in a coordinated (optimized, relevant) manner.

In one embodiment, the system according to the invention comprises at least one drone (1), which drone is piloted by "on-board" or "remote" (or "remotely accessed") software for managing the treatment (e.g. cleaning or dusting).

The software (the steps of the method) makes it possible to manage (e.g. to optimize) the flight trajectories in order to cover the various elements or objects present in the volume of the zone or volume to be treated.

In one embodiment, a state diagram (i.e. the linking together of multiple movement diagrams) is produced in a manner specific to the invention. In one specific embodiment, the drone a) performs pseudo-random movements (which are locally adjusted in real time according to feedback from sensors on board the drone) with b) the additional constraint consisting in maximizing "surface tracking". For example, a low table or the top of an item of furniture may require horizontal surface tracking.

The pseudo-random movements guarantee that the entire zone to be cleaned will be covered after multiple passes and has the advantage that the overall configuration of the zone is not taken into account (i.e. a prior map of the locations is not required). Considering the low level of autonomy of current batteries, surface (e.g. wall, etc.) tracking is energetically efficient. Specifically, the trajectories of the drone that are located "right in the middle" of the volumes to be cleaned are generally useless: no object to be dusted located in the environment is able to levitate and is therefore necessarily in contact with one of the walls of the dwelling (either directly or indirectly, i.e. in contact with a series of other elements, at least one of which is in contact with a wall). Tracking the horizontal surface of a shelf or of a table on which objects are placed also counts as surface tracking. "Surface tracking" is therefore advantageous in terms of optimization (of power, treatment duration).

In one embodiment, the management of the movements of the drone by the system is supported by a software portion implemented on the processor of the smartphone (2), of a computer or of a server. The use of the expression "processor" covers the spatial and/or temporal distribution of computing means (e.g. cloud computing, multicore or manycore processors).

In one embodiment, the environment comprises one or more beacons (3a) so that certain zones are avoided (with a view to protecting fragile objects or else in order to prevent the drone from moving into dangerous locations, for example the surface of a halogen light fitting or lamp as illustrated in the figure). In one embodiment, the beacons comprise LF or HF passive RFID tags or transponders (in various sizes depending on the perimeter to be protected). These transponders or tags are inexpensive, do not take up much space and do not require a power supply. In the case of the environment being provided with such tags, the drone includes one or more tag readers. As illustrated in the figure, a transponder (3a) delimits a zone (3b) that is the maximum detection distance of the reader (FIG. 4 (11)) on board the drone.

Figure 2:
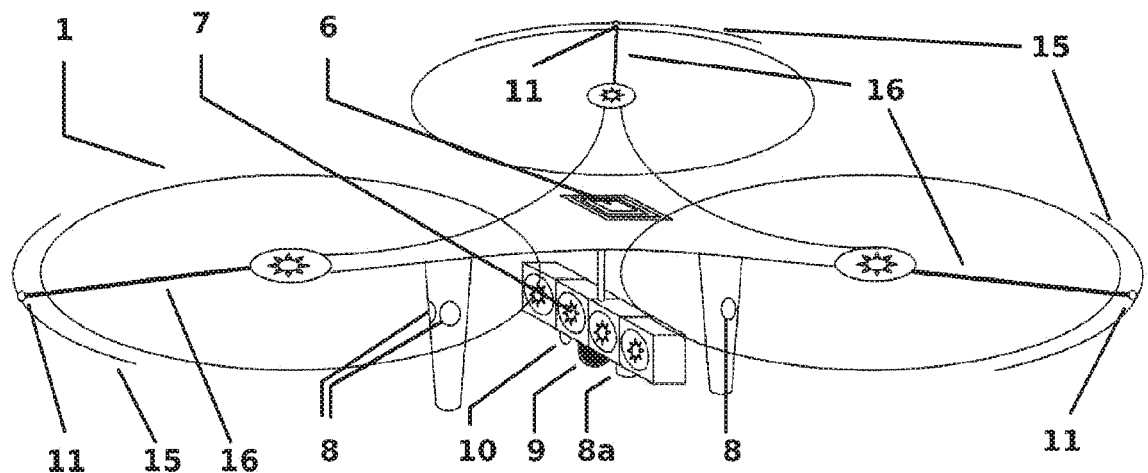
FIG. 2 shows an exemplary embodiment of the drone according to the invention with various sensors and multiple fans arranged in a bar.

In one variant embodiment, a UHF RFID reader and tags (4a) are used to delimit a zone of several meters (4b) that the drone (1) should not leave, the latter being provided this time with a UHF passive RFID transponder (FIG. 2 (6)) for reasons of power consumption. In the example illustrated in FIG. 1, the drone will therefore not be able to fly into the kitchen corner.

FIG. 1 illustrates an optional embodiment in which a robot vacuum cleaner (5) and the drone according to the invention (1) cooperate. In the case of a drone piloted by a system that is not capable of differentiating the floor from other surfaces, a first pass by the robot vacuum cleaner is performed before the drone displaces dust located on the floor. Next, the robot vacuum cleaner returns to be recharged and the drone takes over by linking together multiple passes broken by charging phases, if required by its power autonomy and if a charging base station is in place. Lastly, the robot vacuum cleaner makes another pass in order to collect dust that has newly fallen to the floor.

In the case that the system is capable of indicating to the drone not to concern itself with the floor, the first pass of the robot vacuum cleaner is then not necessary.

In one embodiment, the cleaning phase or sequences are managed "room by room" (for example, the robot vacuum cleaner cleans one room while the drone dusts another).

The cooperation between one or more robot vacuum cleaners and one or more drones according to the invention may be governed and implemented according to various modalities. Coordination rules may for example be dictated by the user via APIs or web services (sequences, conditioned), for example via dedicated home automation web platforms.

In one embodiment, a robot vacuum cleaner may be slaved to the drone according to the invention. Conversely, in one embodiment, the drone according to the invention may be slaved to the robot vacuum cleaner. In one embodiment, a robot vacuum cleaner and a drone according to the invention may communicate bidirectionally. In one embodiment, the charging base station of the drone and/or of the robot vacuum cleaner may intervene in the interaction in order to supervise, inhibit, reinforce, or regulate the interactions. In one embodiment, the interaction diagram is enriched by the presence of a smartphone and/or of a tablet. In other embodiments, more complex diagrams are implemented: a swarm or collection of (potentially miniaturized) robot vacuum cleaners working in concert with a plurality of drones, peer-to-peer communications and negotiations, etc.

FIG. 2 presents an embodiment of wireless dusting or cleaning. In the example, the drone is a trirotor, this shape advantageously allowing movements between objects located in the environment when the latter are separated by a distance that is smaller than the size of the drone (stated otherwise, one of the three portions of the drone may advance between the objects, allowing the distance to be decreased and, potentially, cleaning to be improved). In other embodiments, the drone is a quadrotor (this allows more substantial payloads to be taken on board compared to those allowed by trirotors).

In order to manage the distance from the drone to its immediate environment, the drone may be provided with distance detectors. These sensors may be ultrasound detectors (8 and 8*a*), the number, position and orientation of which make it possible to manage these distances for any volume located below the drone (1) up to within the plane delimited here by its rotors, or even above. In the example of the figure, each of the feet of the drone possesses a pair of ultrasound distance detectors and the center axis of the latter is inclined downward by several degrees in order to complete the field of the distance detector (8*a*) that is located below a bar of fans (7), which will be described in detail below.

Figure 11:
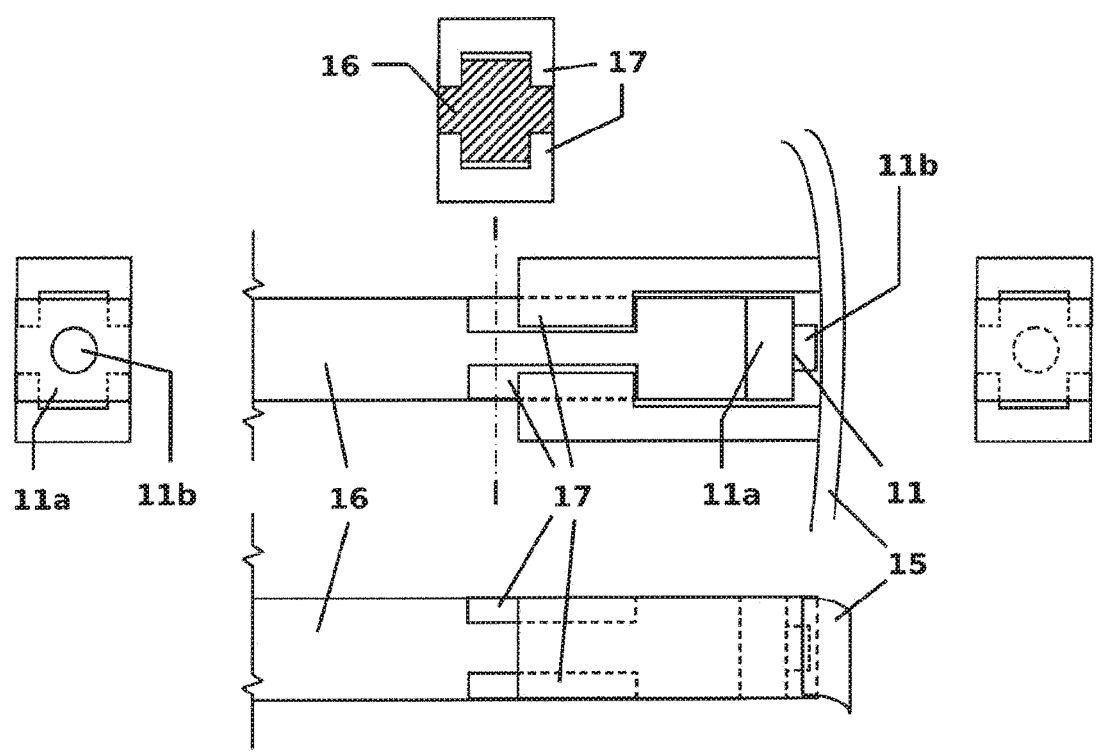
FIG. 11 illustrates the way in which the guards are fastened by means of runners positioned at the ends of the support rods in order to activate the contact sensors if necessary.

In addition to or instead of the distance sensors, the drone (1) may have contact detectors (11) on board, for example detectors of tactile switch type. In one embodiment, the contact detectors (11) are advantageously positioned at the ends of rods (16) to which guards (15) partially surrounding the helices of the drone (1) are fastened. A functional diagram of the way in which the guards apply pressure to the contact detectors when contact is made with elements in the environment is shown in FIG. 11.

Managing the distance from the various portions of the drone to its environment makes it possible for the on-board treatment or cleaning devices to approach objects to be treated up to an optimized distance: not too far away so that the action of the treatment performed is effective and not to close in order to avoid (in particular) the airflow or draught generated by the rotors disrupting the environment.

Figure 3:
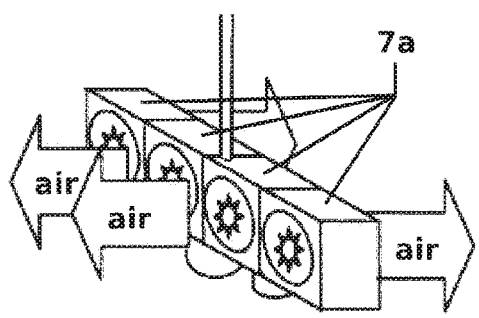
FIG. 3 schematically shows the airflows generated by the on-board fans, illustrating the way in which these flows compensate for one another in order to maintain the stability of the drone.

In one embodiment, in order to displace dust effectively, the drone (1) comprises a system for generating airflows (7). This embodiment is advantageous for dusting for example television screens, window blinds or zones to be treated carefully. In the example, the drone comprises four fans (7*a*). This even number of fans allows, according to certain arrangements, two air flows to be generated on either side, which allows the forces to be balanced out. In one variant embodiment presented in FIG. 3, this arrangement also allows the turning moments to be balanced (the mirror symmetry of the streams balances out the moments) thus avoiding the drone (1) having to intensively compensate for the disruptive force generated by the fans. The starting, stopping and potentially the speed of rotation of these fans (7*a*) may be modulated according to distance measurements made by the ultrasound detectors (8) and/or according to disruptions perceived by the cameras (9). Stated otherwise, the forces generated by the various fans may be fully integrated into the overall trajectory management of the drone. In the absence of the detection of elements in proximity, the fans (7*a*) are generally still, thereby saving battery power.

In one embodiment, the drone includes a single fan. Advantageously, this configuration makes it possible to decrease the power required to supply the fan and to bear it as a payload. According to this configuration, the thrust generated by the single fan is then compensated for by the drone.

The selection of an embodiment with one, two, four, n or 2n fans depends on the specific circumstances (e.g. the presence of a feedback loop for compensating for disruptive forces such as the wind, advantages in terms of power used, etc.).

Figure 4:
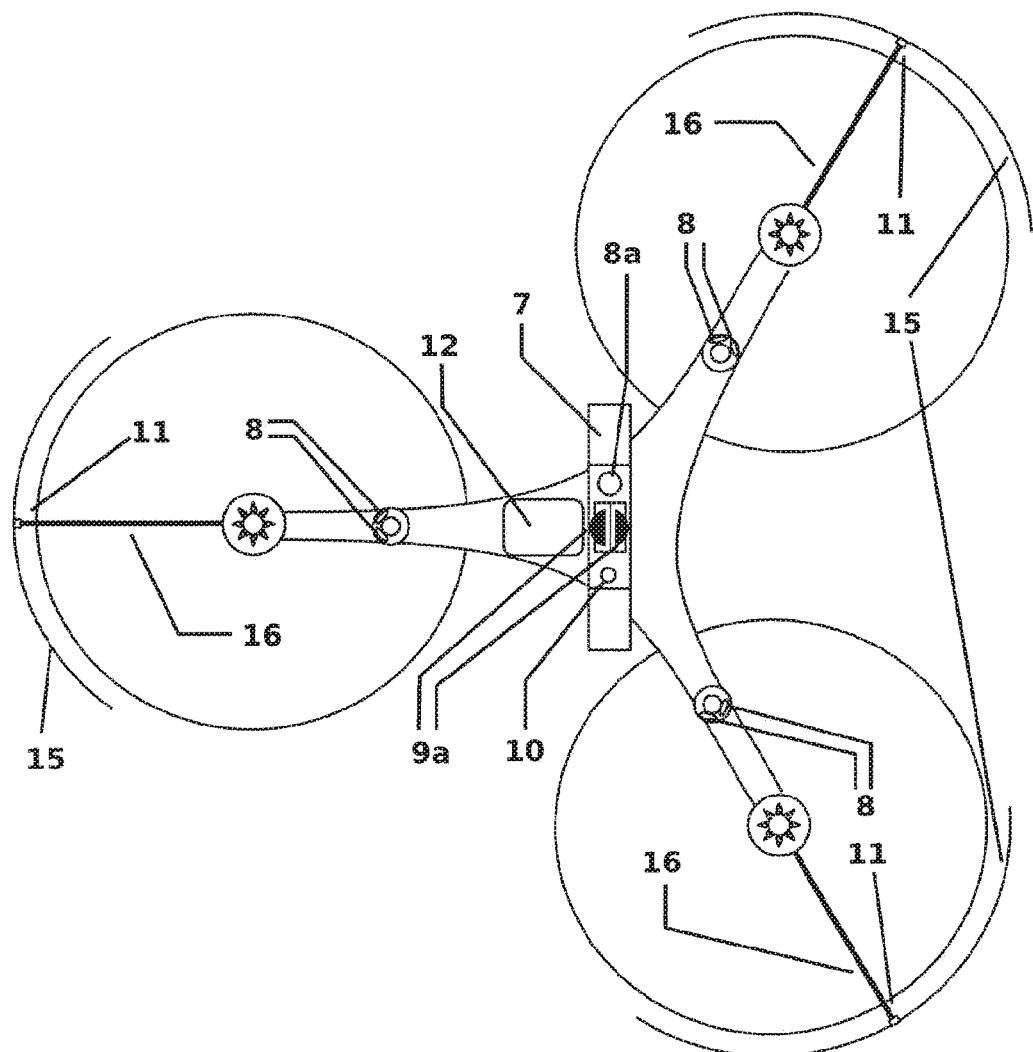
FIG. 4 shows the bottom of a drone according to one specific embodiment, with various on-board sensors and fans.
Figure 5:
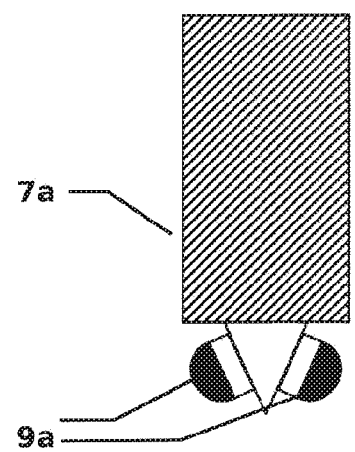
FIG. 5 is a portion of a cross section illustrating an example of the positioning of wide-angle cameras on board the drone.

In one embodiment, so that the drone (1) does not displace elements in its environment by mistake and/or unexpectedly, imagers may be included on board (9). In the example, the cameras (9*a*) illustrated in FIGS. 4 and 5 are endowed with a wide-angle lens (170° or more). Optionally, cameras without near-IR filters may be used, thereby making it possible to use illumination based on LEDs emitting in the near-IR.

By positioning these two cameras (9*a*) below the fans (7*a*) as illustrated in FIG. 5, the visual field being monitored advantageously takes the ends of the rotors of the drone (1) into account in addition to covering the entire scene located below the drone.

The resulting video streams are analyzed. For example, facial detection algorithms allow a distance to be maintained from users who may potentially be present in the room. Motion detection may be carried out, for example in order to determine the presence of sheets of paper that are about to fly away (low table in FIG. 1) or an ornament that is starting to wobble. If the cameras are not provided with internal (optical or digital) image stabilization that is sufficient to compensate for the movements and vibrations of the drone, analysis of the optical flow makes it possible to compensate for most of the movement in the stream of images, thereby making it possible, in a second stage, to detect secondary movements. In this the use of wide-angle cameras has another advantage in that it avoids the movement of elements in the scene that are disrupted by the drone occupying most of the image. As soon as the commencement of such a movement starts to be perceived, it is then possible to decrease the intensity of the dusting operation or to move the drone away. In one embodiment, the cameras may be models provided with an ISP (image signal processor) capable of compressing the video stream on the fly, the latter only having to be transmitted to the control device (for example a smartphone or a computer), the processor of which will carry out the decoding and processing (such as the processing for navigation, facial detection, etc.) justifying the energy spent by the drone for transmitting the video stream. In one embodiment, the intensive video processing operations are carried out by a processor on board the drone.

In one embodiment, the drone has one or more depth-sensing or RGB-D cameras on board. This type of camera advantageously replaces the camera-distance sensor combination by simultaneously allowing distance measurement and motion detection. Some of these cameras, referred to as time-of-flight or TOF cameras, measure the time taken by a near-infrared encoded light pulse to be reflected off surfaces.

FIG. 4 illustrates the presence of an LF or HF RFID detector (12) making it possible to prevent access to the zones delimited by the distances within which the corresponding passive tags ((3a) in FIG. 1) are detected. Placing the RFID detector (12) instead of a passive tag on the drone (1) makes it possible to easily delimit, inexpensively and without being invasive, multiple spatial zones.

Figure 6:
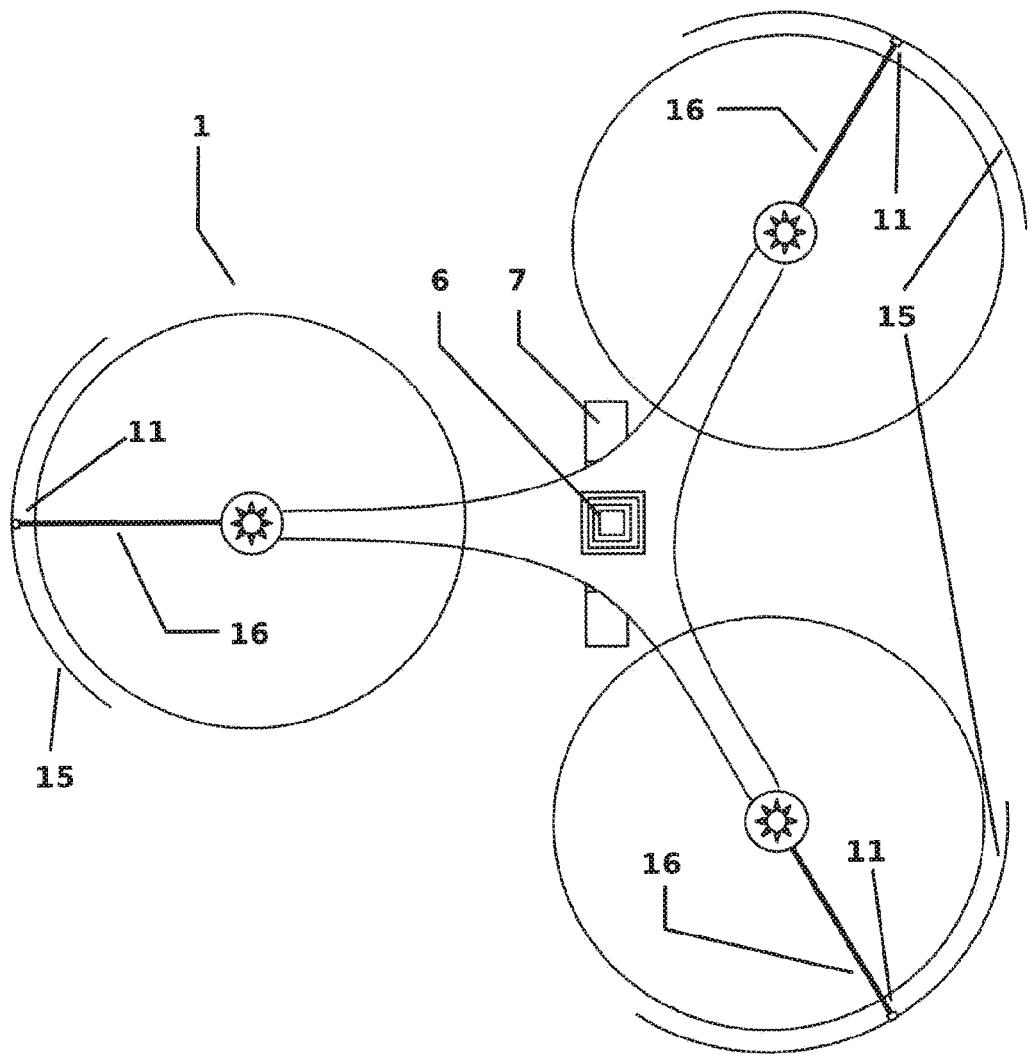
FIG. 6 shows the bottom of a drone according to one specific embodiment with an RFID transponder.

FIGS. 2 and 6 illustrate the presence of a UHF passive tag (6) for preventing the drone (1) from straying too far from the associated UHF medium-range reader ((4a) in FIG. 1). Placing the passive tag on the drone this time addresses power consumption constraints of UHF medium-range readers. In one embodiment, once the passive tag is no longer stimulated by the associated reader, or if the intensity of the signal drops below a specific threshold, the drone "reverses" (or modifies its trajectory" until once again picking up the signal from the reader correctly (above a predefined threshold).

Figure 7:
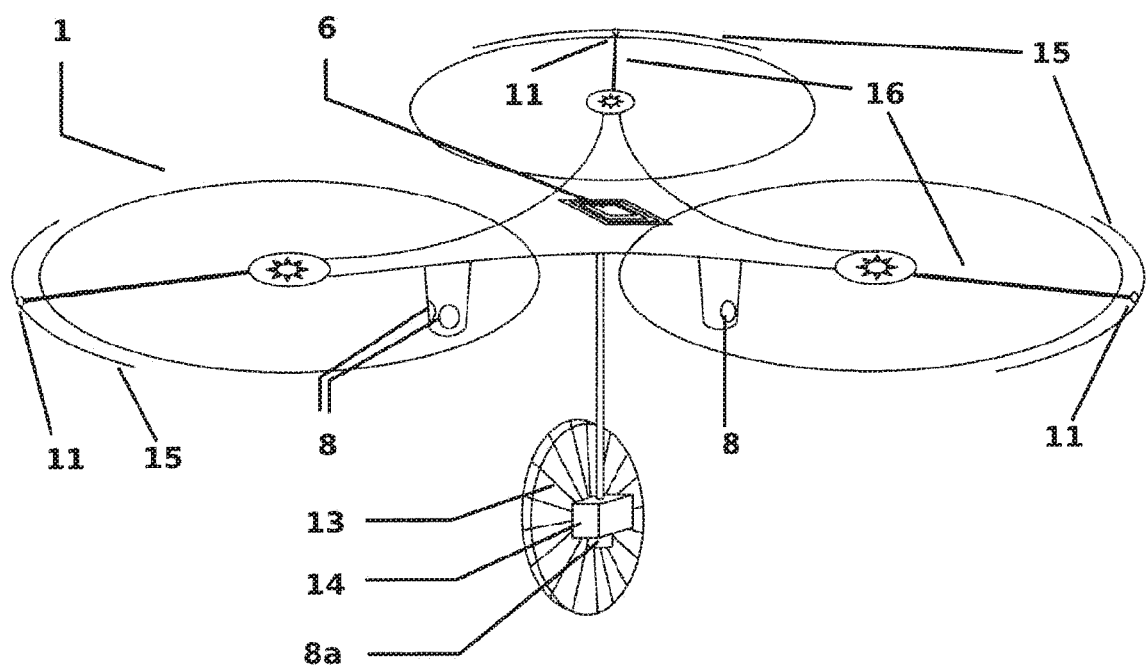
FIG. 7 illustrates one specific embodiment of the drone according to the invention, provided with a rotary brush.

FIG. 7 shows one variant embodiment. The bar of fans ((7) in FIG. 2) is here replaced by a brush (13) fastened to the end of a rod, thus serving as a duster. In order to decrease the accumulation of dust on the latter, and hence its maintenance by the user, the presence of a rotary brush with soft bristles is advantageous.

Figure 8:
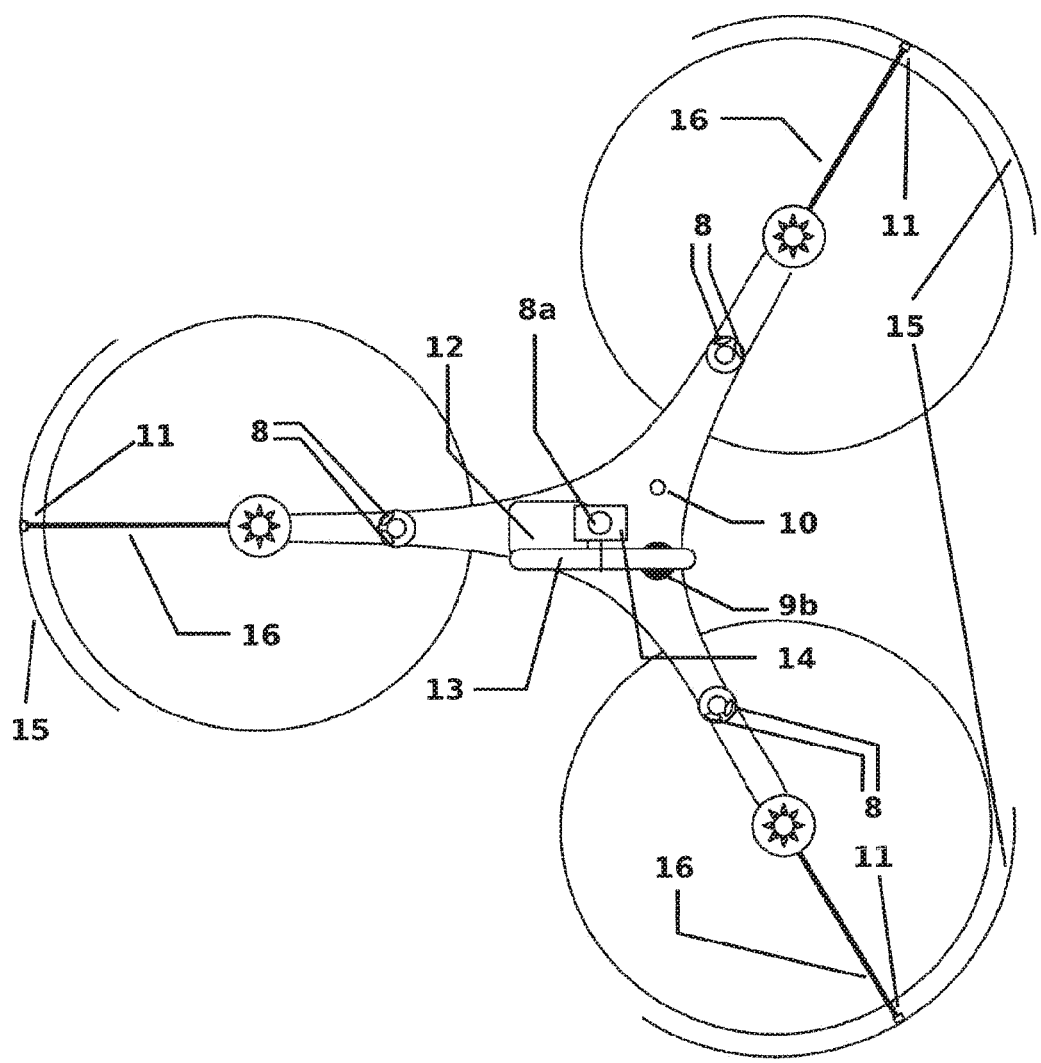
FIG. 8 shows the bottom of the drone according to the preceding embodiment.

FIG. 8 is a view from below of the preceding embodiment.

Figure 9:
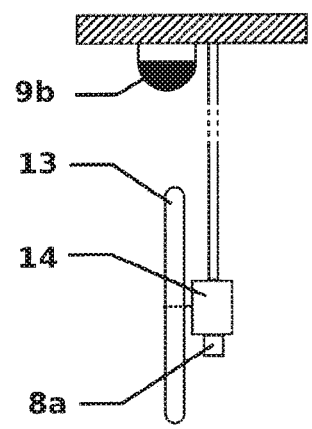
FIG. 9 is a portion of a cross section illustrating an example of the operation of the rotary brush.

FIG. 9 shows a few details of this rotary brush, in particular its motor. In the example, an ultrasound distance detector (8a) is located at the end of a rod descending from the body of the drone (1), below the motor (14) driving the brush. In order to have an overall view allowing both the action of the brush and the effects of the air displaced by the rotors of the drone on the environment to be observed, the motion detection system, responsible for avoiding the displacement of elements in the environment other than dust, is here composed of a single wide-angle camera without a near-infrared filter (9b) located below the body of the drone, and hence above the assembly shown in detail in FIG. 9 composed of the soft-bristled brush (13), its motor (14) and the ultrasound distance detector (8a). Similarly, the near-infrared LED lighting system (10) shown in FIG. 8 is itself also positioned directly below the body of the drone. In one embodiment, the initiation of rotation and/or the speed of rotation of the brush may be regulated by measurements arising from the distance detectors (for example ultrasound detectors (8 and 8a)) and/or the motion detection system (9b).

Figure 10:
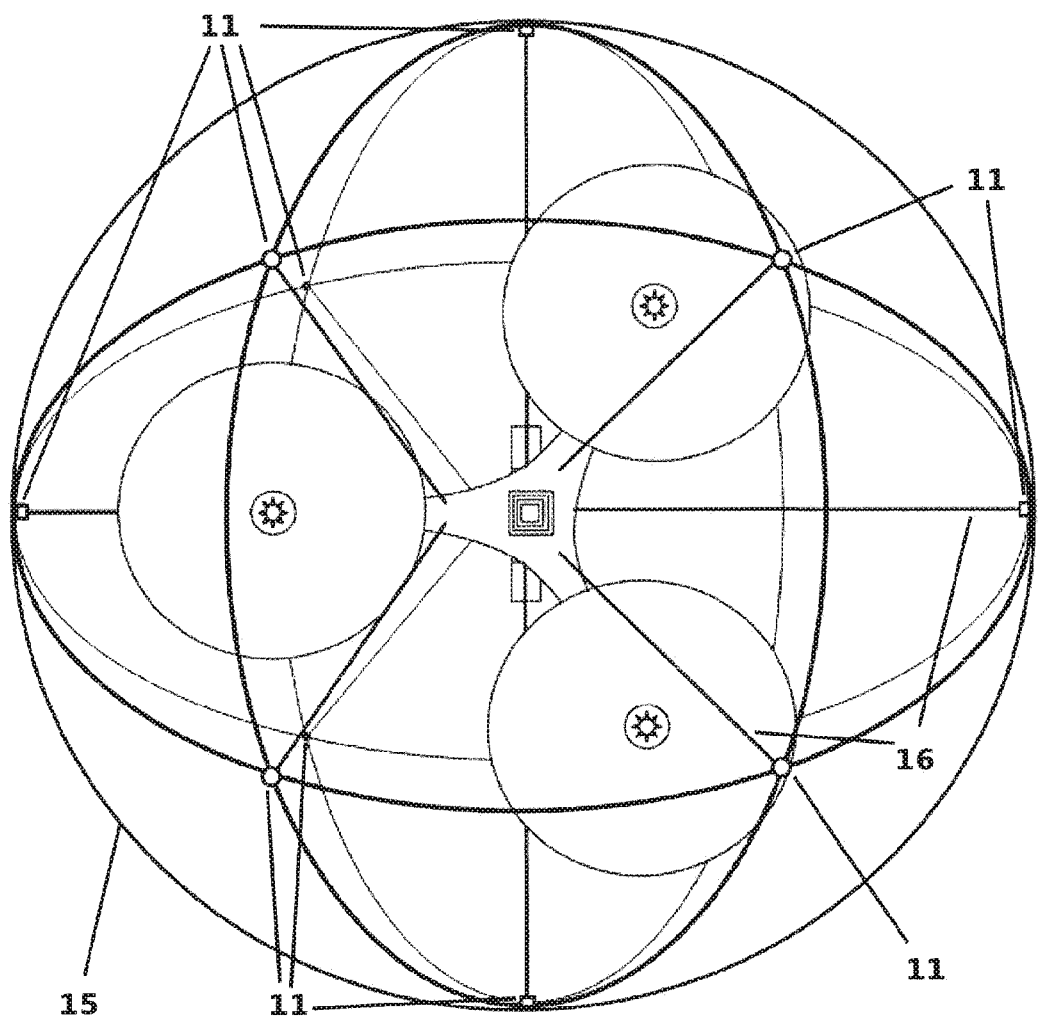
FIG. 10 shows a variant embodiment of the drone according to the invention including contact sensors and safety guards.

FIG. 10 presents one variant embodiment. In the example, the minimum distance from the drone to elements in its vicinity is physically ensured by guards (15) made of plastic (completely or partially surrounding it), which guards are optionally provided with contact detectors (11). These contact detectors (for example of tactile switch type) serve to prevent the drone from following its trajectory in the direction in which contact with an element in this environment has been detected. It is then possible to do away with ultrasound distance detectors.

FIG. 11 illustrates the operation of the tactile switches (11) when one of the guards (15) comes into contact with one of the elements or objects in the environment. The contact detectors (11) are composed of a base (11a) fastened to the end of the rods (16) holding the guards (15) around the body of the drone. The button (11b) is depressed into this base (11a) when it is pressed by the portion of the guard (15) located in front of it, and in so doing it then indicates that it is being pressed like with the keys of a keyboard. It is possible for the guards (15) to press the buttons of the contact detectors (11b) due to the presence of runners (17) that allow a limited displacement along the rod (16). Since the contact detectors are advantageously positioned at multiple locations on the drone, pressing any portion of one of the guards will be transmitted to the contact detectors in proximity.

In other embodiments, the contact detectors may be replaced by other detection means, for example by applying one or more sensitive membranes over the guards, allowing the sense of touch to be obtained (e.g. "artificial skin", or adding a membrane allowing a sense of touch to be obtained via the analysis of the propagation of waves generated by contact, etc.).

The invention claimed is:

1. A computer-implemented method for managing the flight of a drone, said drone comprising a physical treatment device, the method comprising the steps repeated over time of:

measuring the distance between the drone and an object present in the environment of the drone;

adjusting the distance from the drone to the object according to predefined internal parameters and external parameters associated with the object present in the environment; and performing a physical treatment on the object from the drone.

2. The method as claimed in claim 1, the external parameters associated with the object comprising a maximum distance beyond which the physical treatment performed by the drone on the object is below a predefined threshold.

3. The method as claimed in claim 1, the external parameters associated with the object being determined by object recognition.

4. The method as claimed in claim 1, the external parameters being determined after receiving the signal from one or more radiofrequency beacons placed in the object or the environment.

5. The method as claimed in claim 1, the physical treatment performed on the object by the drone comprising one or more treatments chosen from a dusting treatment and a sterilization treatment.

6. A computer program product, said computer program comprising code instructions allowing the steps of the method as claimed in claim 1 to be carried out, when said program is executed on a computer.

7. A system comprising:

at least one drone including:

a physical treatment device for dusting and/or sterilizing one or more objects present in the environment, the physical treatment device beside a propulsion system, the physical treatment device configured to generate an airflow in a direction that is substantially non-parallel to the axis of sustentation and/or of propulsion of the drone, and a measurement device configured to allow the distance between the drone and an object present in the environment to be adjusted, wherein the system is configured to:
  measure the distance between the drone and the object present in the environment of the drone;
  adjust the distance from the drone to the object according to predefined internal parameters and external parameters associated with the object present in the environment; and
  perform a physical treatment on the object from the drone.

8. The system as claimed in claim 7, the drone comprising one or more devices for generating airflows that are arranged so as to allow a static or dynamic equilibrium in terms of force and/or in terms of moment.

9. The system as claimed in claim 7, the measurement device comprising one or more sensors selected from position sensors, distance sensors, contact sensors and sensors for detecting motion.

10. The system as claimed in claim 7, the measurement device comprising a camera.

11. The system as claimed in claim 7, the physical treatment device comprising at least one fan.

12. The system as claimed in claim 7, the physical treatment device comprising a motorized brush and/or a duster.

13. The system as claimed in claim 7, the physical treatment device comprising a sterilizer or a germicidal lamp.

14. The system as claimed in claim 7, the drone being autonomous.

15. The system as claimed in claim 7, comprising a plurality of drones.

16. The system as claimed in claim 7, further comprising at least one floor-cleaning robot.

* * * * *